(12) United States Patent
Henderson

(10) Patent No.: US 11,464,945 B1
(45) Date of Patent: Oct. 11, 2022

(54) CATHETER CANAL

(71) Applicant: Willie Henderson, Henderson, NV (US)

(72) Inventor: Willie Henderson, Henderson, NV (US)

( * ) Notice: Subject to any disclaimer, the term of this patent is extended or adjusted under 35 U.S.C. 154(b) by 121 days.

(21) Appl. No.: 16/922,054

(22) Filed: Jul. 7, 2020

(51) Int. Cl.
| | |
|---|---|
| *A61M 25/01* | (2006.01) |
| *A61M 25/09* | (2006.01) |
| *A61M 25/02* | (2006.01) |
| *A61M 25/00* | (2006.01) |

(52) U.S. Cl.
CPC .... *A61M 25/0147* (2013.01); *A61M 25/0021* (2013.01); *A61M 25/0141* (2013.01); *A61M 25/09* (2013.01); *A61M 2025/0253* (2013.01); *A61M 2205/02* (2013.01); *A61M 2210/125* (2013.01)

(58) Field of Classification Search
CPC ... A47B 2097/003; Y10T 24/13; Y10T 24/33; F16L 3/02; F16L 3/04; F16L 3/06; F16L 3/1226; F16L 3/123; A61M 25/01; A61M 25/0113; A61M 25/0668; A61M 25/0662; A61M 2025/0681; A61M 2025/0246; A61M 2025/028; A61M 2005/1586; A61M 25/02; A61M 2210/04
See application file for complete search history.

(56) References Cited

U.S. PATENT DOCUMENTS

| | | | | |
|---|---|---|---|---|
| 1,670,347 A | * | 5/1928 | Gordon | F16L 3/1226 24/115 A |
| 3,659,319 A | * | 5/1972 | Erickson | F16L 3/13 24/304 |
| 4,224,937 A | * | 9/1980 | Gordon | A61M 25/02 604/180 |
| 5,323,992 A | * | 6/1994 | Sifers | A61M 5/1418 24/129 R |
| 5,417,668 A | | 5/1995 | Setzer | |
| 5,523,529 A | * | 6/1996 | Holliday | H02G 3/0418 138/163 |
| 5,690,617 A | * | 11/1997 | Wright | A61M 25/02 128/DIG. 26 |

(Continued)

FOREIGN PATENT DOCUMENTS

| | | | | |
|---|---|---|---|---|
| CN | 102474085 B | * | 11/2015 | F16L 3/08 |
| CN | 108378988 A | * | 8/2018 | |

(Continued)

*Primary Examiner* — Jason E Flick
*Assistant Examiner* — Adam J. Cermak
(74) *Attorney, Agent, or Firm* — Kyle A. Fletcher, Esq.

(57) ABSTRACT

The catheter canal is a medical device. The catheter canal is configured for use with a guiding catheter or guide sheath. The catheter canal forms a canal that controls and eliminates potentially undesirable movement of a catheter, wire, stent, balloon or any other over the wire instrument as it is inserted into a patient. The catheter canal includes a guiding structure, a plurality of flexible structures, and an adhesive structure. The plurality of flexible structures and the adhesive structure attaches to the guiding structure. The plurality of flexible structures form a framework that creates the canal that controls and limits potentially undesirable movement of the catheter, wire, stent, balloon or any other over the wire instrument.

15 Claims, 4 Drawing Sheets

(56) References Cited

U.S. PATENT DOCUMENTS

| | | | |
|---|---|---|---|
| 5,795,335 A * | 8/1998 | Zinreich | A61M 25/02 604/174 |
| 5,971,991 A * | 10/1999 | Sunderland | A61M 25/0113 606/108 |
| 6,311,933 B1 | 11/2001 | Starchevich | |
| 6,432,121 B1 * | 8/2002 | Jervis | A61B 17/00234 606/190 |
| 6,567,602 B2 * | 5/2003 | Cole | G02B 6/4459 385/136 |
| 6,749,601 B2 | 6/2004 | Chin | |
| 7,434,769 B1 * | 10/2008 | May | F16M 11/10 174/68.1 |
| 8,795,238 B2 | 8/2014 | Cady | |
| 8,882,718 B2 | 11/2014 | Mullet | |
| 9,265,345 B2 * | 2/2016 | Lindblom | F16L 3/02 |
| D756,510 S | 5/2016 | Fitzgerald | |
| 9,598,028 B2 * | 3/2017 | Renner | H02G 3/0608 |
| 10,780,214 B1 * | 9/2020 | Hensler | A61M 5/142 |
| 10,786,652 B2 * | 9/2020 | Doshi | A61F 13/0216 |
| 11,258,240 B1 * | 2/2022 | White | H02G 3/30 |
| 2005/0004553 A1 | 1/2005 | Douk | |
| 2005/0218269 A1 * | 10/2005 | Franks | F16L 3/1226 248/63 |
| 2005/0277888 A1 * | 12/2005 | Propp | A61M 25/02 604/174 |
| 2008/0045892 A1 * | 2/2008 | Ferry | A61M 25/0113 604/95.01 |
| 2010/0274250 A1 * | 10/2010 | Wallace | A61B 17/025 606/79 |
| 2011/0030832 A1 * | 2/2011 | Larson | F16L 3/08 138/137 |
| 2012/0041378 A1 * | 2/2012 | Bierman | A61M 25/02 604/180 |
| 2013/0165863 A1 * | 6/2013 | Nilson | A61M 25/02 604/180 |
| 2014/0031788 A1 * | 1/2014 | Sung | A61B 17/3415 604/506 |
| 2014/0060547 A1 * | 3/2014 | Vallino | A61F 5/3761 128/845 |
| 2014/0148778 A1 * | 5/2014 | Levy | A61M 25/02 604/500 |
| 2015/0187460 A1 * | 7/2015 | DeLoache | A47B 21/06 248/68.1 |
| 2016/0095597 A1 * | 4/2016 | Belson | A61B 17/08 604/21 |
| 2016/0279397 A1 * | 9/2016 | Katra | A61M 25/0668 |
| 2017/0203079 A1 * | 7/2017 | Harris | A61M 25/02 |
| 2017/0281344 A1 * | 10/2017 | Costello | A61M 25/0133 |
| 2019/0001101 A1 * | 1/2019 | Hsu | A61M 25/02 |
| 2019/0307587 A1 * | 10/2019 | Fargahi | A61F 2/2418 |
| 2020/0016374 A1 * | 1/2020 | Burkholz | A61M 25/0111 |
| 2020/0268413 A1 * | 8/2020 | Khalaj | A61B 17/3415 |
| 2021/0001086 A1 * | 1/2021 | Berul | A61M 25/0113 |
| 2021/0045771 A1 * | 2/2021 | Gibertoni | A61B 17/3496 |
| 2021/0260345 A1 * | 8/2021 | Burkholz | A61M 25/0111 |

FOREIGN PATENT DOCUMENTS

| | | | | |
|---|---|---|---|---|
| CN | 109152616 A | * | 1/2019 | G21F 3/00 |
| CN | 110049739 A | * | 7/2019 | A61M 25/09041 |
| CN | 113425941 A | * | 9/2021 | A61B 5/154 |
| CN | 114175419 A | * | 3/2022 | A47B 96/067 |
| DE | 19602477 C1 | * | 7/1997 | H02G 3/0481 |
| DE | 202011101535 U1 | * | 9/2012 | A61M 25/09041 |
| DE | 102016003692 A1 | * | 9/2017 | H02G 3/0456 |
| EP | 2195063 B1 | * | 8/2019 | A61M 39/06 |
| GB | 190905635 A | * | 2/1910 | F16L 3/06 |
| GB | 2233163 A | * | 1/1991 | H02G 3/0468 |
| GB | 2328995 A | * | 3/1999 | A61M 25/02 |
| JP | 2002360705 A | * | 12/2002 | A61M 25/02 |
| JP | 2021122731 A | * | 8/2021 | A61F 2/95 |
| SE | 1200327 A1 | * | 11/2013 | A61M 25/02 |
| WO | WO-0029056 A2 | * | 5/2000 | A61M 25/0041 |
| WO | 2005002658 | | 1/2005 | |
| WO | WO-2007123770 A2 | * | 11/2007 | A61M 25/0113 |
| WO | WO-2009064639 A1 | * | 5/2009 | F16L 3/06 |
| WO | WO-2011059728 A2 | * | 5/2011 | A61M 25/02 |
| WO | WO-2020109448 A1 | * | 6/2020 | A61M 25/0606 |
| WO | WO-2020162870 A1 | * | 8/2020 | B32B 1/08 |
| WO | WO-2021105415 A1 | * | 6/2021 | A61M 25/02 |
| WO | WO-2021146621 A | * | 7/2021 | A61M 25/01 |

* cited by examiner

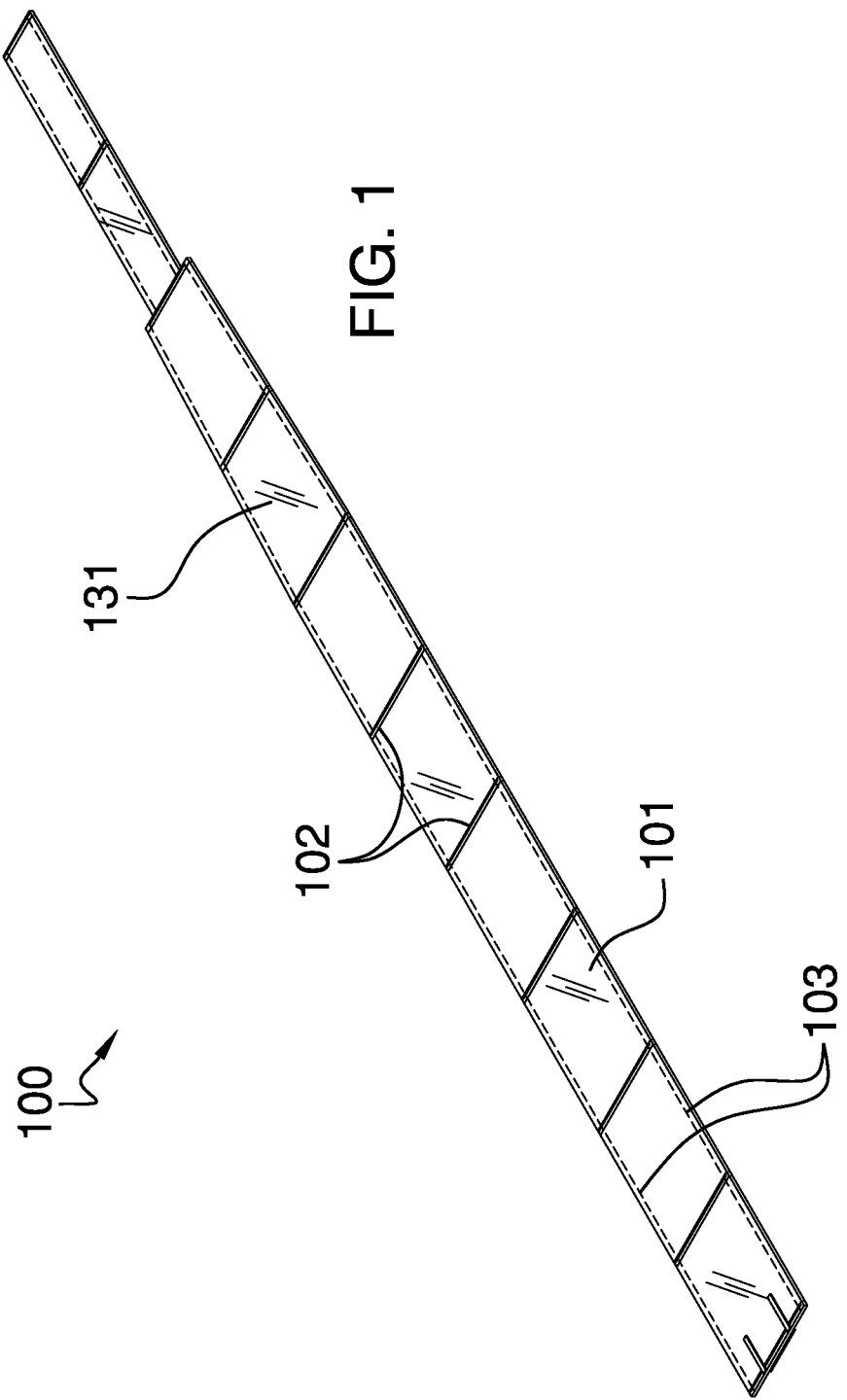

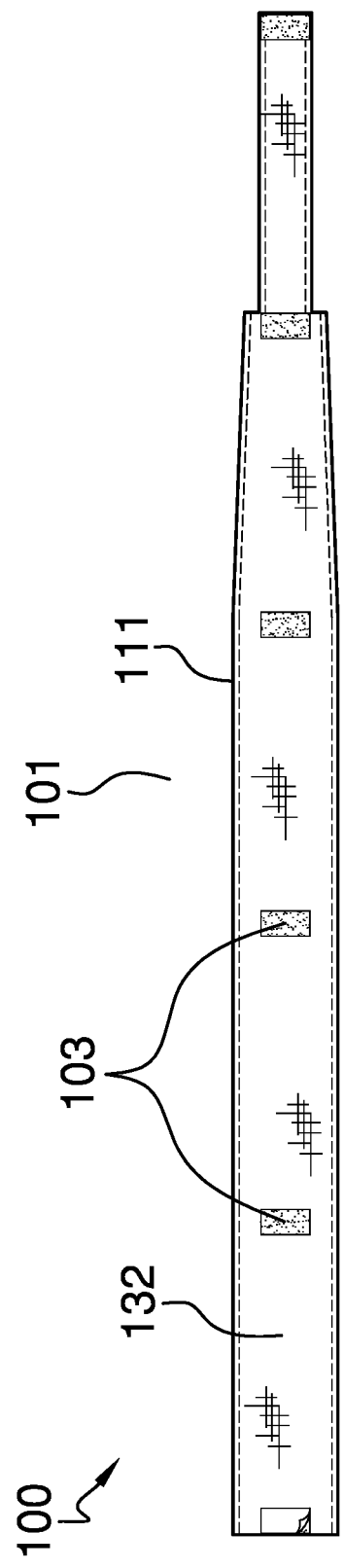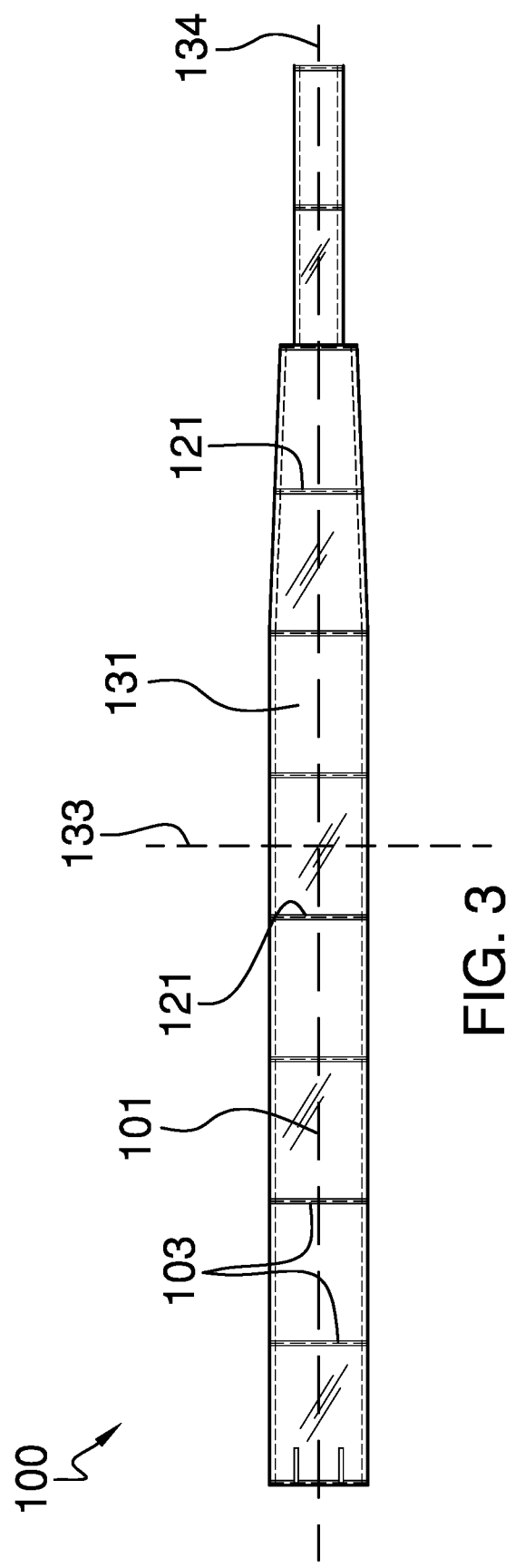

CATHETER CANAL

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical science including devices for introducing equipment and instruments into a body's arterial and venous system, more specifically, a cardiovascular intervention kit.

SUMMARY OF INVENTION

The catheter canal is a medical device. The catheter canal is configured for use with a guiding catheter or guide sheath. The catheter canal forms a canal that controls and eliminates potentially undesirable movement of a catheter, wire, stent, balloon or any other over the wire instrument as it is inserted into a patient. The catheter canal comprises a guiding structure, a plurality of flexible structures, and an adhesive structure. The plurality of flexible structures and the adhesive structure attaches to the guiding structure. The plurality of flexible structures form a framework that creates the canal that controls and limits potentially undesirable movement of the catheter, wire, stent, balloon or any other over the wire instrument. The adhesive structure secures the catheter canal in a fixed position during the insertion of the catheter, wire, stent, balloon or any other over the wire instrument into the patient.

These together with additional objects, features and advantages of the catheter canal will be readily apparent to those of ordinary skill in the art upon reading the following detailed description of the presently preferred, but nonetheless illustrative, embodiments when taken in conjunction with the accompanying drawings.

In this respect, before explaining the current embodiments of the catheter canal in detail, it is to be understood that the catheter canal is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the catheter canal.

It is therefore important that the claims be regarded as including such equivalent construction insofar as they do not depart from the spirit and scope of the catheter canal. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 1 is a perspective view of an embodiment of the disclosure.

FIG. 2 is a bottom view of an embodiment of the disclosure.

FIG. 3 is a top view of an embodiment of the disclosure.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 4:
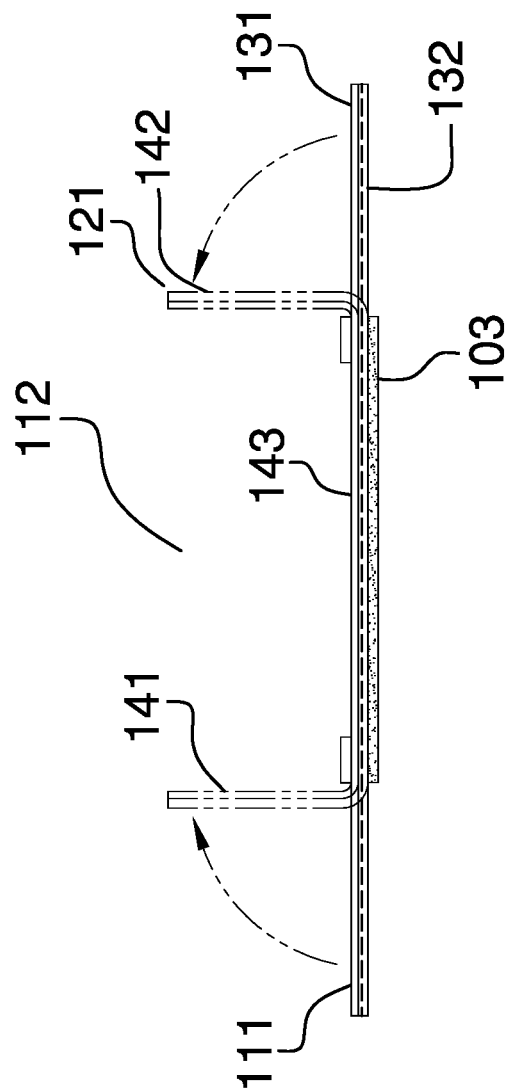
FIG. 4 is an end view of an embodiment of the disclosure.
Figure 5:
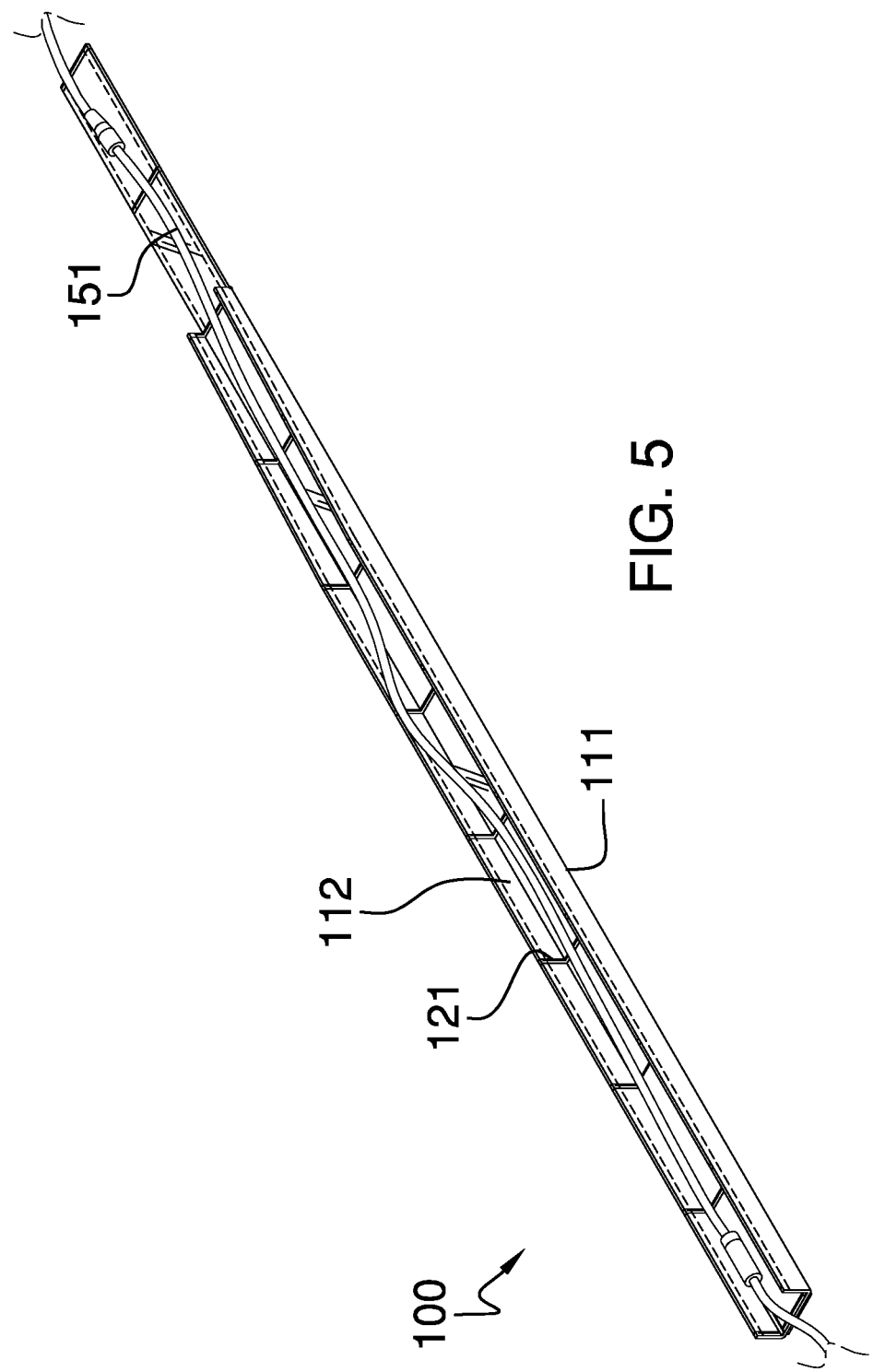
FIG. 5 is an in-use view of an embodiment of the disclosure.

Detailed reference will now be made to one or more potential embodiments of the disclosure, which are illustrated in FIGS. 1 through 5.

The catheter canal 100 (hereinafter invention) is a medical device. The invention 100 is configured for use with a catheter, wire, stent, balloon or any other over the wire instrument 151 (hereinafter catheter). The invention 100 forms a canal that controls and eliminates potentially undesirable movement of the catheter 151 as it is inserted into a patient. The invention 100 comprises a guiding structure 101, a plurality of flexible structures 102, and an adhesive structure 103. The plurality of flexible structures 102 and the adhesive structure 103 attaches to the guiding structure 101. The plurality of flexible structures 102 form a framework that creates the canal that controls and limits potentially undesirable movement of the catheter 151. The adhesive structure 103 secures the invention 100 in a fixed position during the insertion of the catheter 151 into the patient.

The catheter 151 is a medical device. The catheter 151 is placed within the canal that controls and limits potentially undesirable movement of the catheter 151 during the medical procedure. The catheter 151 is defined elsewhere in this disclosure.

The guiding structure 101 is a structure. The guiding structure 101 is a flexible structure with an inelastic nature. The guiding structure 101 forms the containment surfaces of the canal that controls and limits potentially undesirable movement of the catheter 151. The guiding structure 101 comprises a sheeting structure 111 and a c-channel 112.

The sheeting structure 111 is a sheeting. The sheeting structure 111 is a flexible structure with an inelastic nature. The sheeting structure 111 physically forms the containment surfaces of the canal that controls and limits potentially undesirable movement of the catheter 151. The sheeting structure 111 attaches to the plurality of flexible structures 102 such that the plurality of flexible structures 102 shapes the sheeting structure 111 into the c-channel 112.

The sheeting structure 111 is cut into the shape of a tapered structure. The term taper is defined elsewhere in this disclosure. The tapered shape of the sheeting structure 111 is determined such that the canal that controls and limits potentially undesirable movement of the catheter 151 more tightly constrains the potentially undesirable motion of the catheter 151 at the position where the catheter 151 is closest to the patient. The sheeting structure 111 comprises a channel surface 131, an attachment surface 132, a major axis 133, and a minor axis 134.

The channel surface 131 is the surface of the sheeting structure 111 that is proximal to the catheter 151 when the invention 100 is used normally. The channel surface 131 forms the interior surface of the canal formed by the c-channel 112. The attachment surface 132 is the surface of the c-channel 112 that is distal from the channel surface 131. The attachment surface 132 forms the exterior surface of the canal formed by the c-channel 112.

The major axis 133 is the major axis 133 of the tapered structure form of the sheeting structure 111. The major axis 133 bisects the space between the edge of the perimeter of the sheeting structure 111 with the greatest span of length and the edge of the perimeter of the sheeting structure 111 that is distal from the edge of the perimeter of the sheeting structure 111 with the greatest span of length. The minor axis 134 is the minor axis 134 of the tapered structure form of the sheeting structure 111. The major axis 133 and the minor axis 134 are defined elsewhere in this disclosure.

The c-channel 112 is a mechanical structure that forms the c-channel 112 that forms the physical individual flexible structures 121. The plurality of flexible structures 102 are deformed such that the sheeting structure 111 is shaped into the boundary structures of the c-channel 112 formed by the guiding structure 101. The c-channel 112 is defined elsewhere in this disclosure.

In the first potential embodiment of the disclosure, the sheeting structure 111 is formed as a fluid impermeable structure. The sheeting structure 111 is formed from a polyurethane.

Each of the plurality of flexible structures 102 is a semi-rigid mechanical structure. Each of the plurality of flexible structures 102 is a flexible structure with an inelastic nature. Each of the plurality of flexible structures 102 is deformed to form a u-shaped structure. The u-shaped structure is defined elsewhere in this disclosure. Each of the plurality of flexible structures 102 attaches to a face of the sheeting structure 111 selected from the group consisting of the channel surface 131 and the attachment surface 132. The plurality of flexible structures 102 forms the framework that shapes the c-channel 112 formed by the guiding structure 101. Each of the plurality of flexible structures 102 is formed from a wire that is bent into the u-shaped structure. The plurality of flexible structures 102 comprises a collection of individual flexible structures 121.

The individual flexible structure 121 is a metal wire structure. The individual flexible structure 121 is a flexible structure with an inelastic nature. Each of the individual flexible structure 121 selected from the plurality of flexible structures 102 are identical. Each individual flexible structure 121 initially attaches to the sheeting structure 111 with the form factor of a Euclidean prism-shaped structure.

Each individual flexible structure 121 is deformed into a non-Euclidean structure to form the c-channel 112 of the guiding structure 101. Specifically, each individual flexible structure 121 is deformed into a u-shaped structure such that the individual flexible structure 121 will deform the sheeting structure 111 in a manner that forms the boundaries of the c-channel 112 formed by the guiding structure 101. Each of the individual flexible structure 121 attaches to the channel surface 131 of the guiding structure 101 such that the center axis of the prism structure of the individual flexible structure 121 is perpendicular to the major axis 133 of the sheeting structure 111.

The individual flexible structure 121 comprises a first arm 141, a second arm 142, and a crossbeam 143.

The first arm 141 is a prism-shaped structure. The first arm 141 is a first arm 141 of the u-shaped structure. The first arm 141 attaches to the crossbeam 143 in the manner of a cantilever. The position of the first arm 141 is set such that the free end of the cantilever structure of the first arm 141 is proximal to the edge of the perimeter of the sheeting structure 111 with the greatest span of length. The second arm 142 is a prism-shaped structure. The second arm 142 is a second arm 142 of the u-shaped structure. The second arm 142 attaches to the crossbeam 143 in the manner of a cantilever. The position of the second arm 142 is set such that the free end of the cantilever structure of the second arm 142 is proximal to the edge of the perimeter of the sheeting structure 111 that is distal from the edge of the perimeter of the sheeting structure 111 with the greatest span of length.

The crossbeam 143 is a prism-shaped structure. The first arm 141 and the second arm 142 attach to the crossbeam 143 in the manner of a cantilever. The crossbeam 143 attaches to the sheeting structure 111 such that the center axis of the prism structure of the crossbeam 143 is perpendicular to the major axis 133 of the sheeting structure 111. The crossbeam 143 attaches to the sheeting structure 111 such that the center axis of the prism structure of the crossbeam 143 is parallel to the minor axis 134 of the sheeting structure 111.

The adhesive structure 103 is a removable adhesive compound. The adhesive and the removable adhesive are defined elsewhere in this disclosure. The adhesive structure 103 forms a coating on the attachment surface 132 of the sheeting structure 111 of the guiding structure 101. The adhesive structure 103 removably attaches the c-channel 112 of the guiding structure 101 to a surface such that the canal that controls and limits potentially undesirable movement of the catheter 151 will not shift during a medical procedure.

The following definitions were used in this disclosure:

C-Channel: As used in this disclosure, the C-channel is a structure that is formed in a U-shape. The C-channel forms a prism shape with a hollow interior and an open face that forms a shape characteristic of the letter C. The open space of the C-channel is often used as a canal.

Cantilever: As used in this disclosure, a cantilever is a beam or other structure that projects away from an object and is supported on only one end. A cantilever is further defined with a fixed end and a free end. The fixed end is the end of the cantilever that is attached to the object. The free end is the end of the cantilever that is distal from the fixed end.

Carbamate: As used in this disclosure, a carbamate is a functional group consisting of an O–(C=O)–N structure. Carbamate is informally referred to as urethane.

Catheter: As used in this disclosure, a catheter is a flexible tube that is inserted into the body through which images may be captured and fluids may be introduced into or removed from the body. Endoscope is a synonym for catheter.

Copolymer: As used in this disclosure, a copolymer is a polymer formed from two or more repeating molecules (also referred to as monomers).

Cord: As used in this disclosure, a cord is a long, thin, flexible, and prism shaped string, line, rope, or wire. Cords are made from yarns, piles, or strands of material that are braided or twisted together or from a monofilament (such as fishing line). Cords have tensile strength but are too flexible to provide compressive strength and are not suitable for use in pushing objects. String, line, cable, and rope are synonyms for cord.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Elastic Nature: As used in this disclosure, an elastic nature refers to a flexible structure that returns to its relaxed shape after the flexible structure has been deformed.

Flexible: As used in this disclosure, flexible refers to an object or material that will deform when a force is applied to it but that will not necessarily return to its original shape when the deforming force is removed.

Form Factor: As used in this disclosure, the term form factor refers to the size and shape of an object.

Frame: As used in this disclosure, a frame is a structure or a first sub-structure: a) to which an object or a second sub-structure attaches; and, b) which forms a portion of the load path of the object or the second sub-structure.

Framework: As used in this disclosure, a framework refers to the substructure of an object that carries the load path of the object.

Inelastic Nature: As used in this disclosure, an inelastic nature refers to a flexible structure that maintains its new shape after the flexible structure has been deformed.

Major and Minor Axes: As used in this disclosure, the major and minor axes refer to a pair of perpendicular axes that are defined within a structure. The length of the major axis is always greater than or equal to the length of the minor axis. The major axis is always the longest diameter of the structure. The major and minor axes intersect at the center of the structure. The major axis is always parallel to the longest edge of a rectangular structure.

Monomer: As used in this disclosure, a monomer refers to a molecular structure that bonds to itself in a repeating manner to form a polymer.

Non-Euclidean Prism: As used in this disclosure, a non-Euclidean prism is a prism structure wherein the center axis of the prism lies on a non-Euclidean plane or is otherwise formed with a curvature.

Patient: As used in this disclosure, a patient is a person who is designated to receive a medical treatment, therapy or service. The term patient may be extended to an animal when used within the context of the animal receiving veterinary treatment or services.

Polymer: As used in this disclosure, a polymer refers to a molecular chain that comprises multiple repeating units known as monomers. The repeating unit may be an atom or a molecular structure.

Polyurethane: As used in this disclosure, a polyurethane is a copolymer wherein the one or more monomer chains are linked together carbamates.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Relaxed Shape: As used in this disclosure, a structure is considered to be in its relaxed state when no shear, strain, or torsional forces are being applied to the structure.

Semi-Rigid Structure: As used in this disclosure, a semi-rigid structure is a solid structure that is stiff but not wholly inflexible and that will deform under force before breaking. A semi-rigid structure may or may not behave with an elastic nature in that a semi-rigid structure need not return to its relaxed shape.

Sheeting: As used in this disclosure, a sheeting is a material, such as a paper, textile, a plastic, or a metal foil, in the form of a thin flexible layer or layers. The sheeting forms a disk structure. The two surfaces of the sheeting with the greatest surface area are called the faces of the sheeting.

Taper: As used in this disclosure, a taper is a change in the span of the length of a structure in the direction parallel to the minor axis of the structure that occurs as an apparent function of the measurement position along the major axis of the object.

Canal: As used in this disclosure, a canal is a physical structural relationship between a first object and a second object that serves a purpose selected from the group consisting of: 1) fastening the second object to the first object; 2) controlling the path of motion of the first object relative to the second object in at least one dimension and in a maximum of two dimensions; or, 3) a combination of the first two elements of this group.

U-Shaped Structure: As used in this disclosure, a U-shaped structure refers to a three-sided structure comprising a crossbeam, a first arm, and a second arm. In a U-shaped structure, the first arm and the second arm project away from the crossbeam: 1) in the same direction; 2) at a roughly perpendicular angle to the crossbeam, and, 3) the span of the length of the first arm roughly equals the span of the length of the second arm. The first arm and the second arm project away from the crossbeam in the manner of a cantilever.

Wire: As used in this disclosure, a wire is a structure with the general appearance of a cord or strand that is formed from an electrically conductive metal.

With respect to the above description, it is to be realized that the optimum dimensional relationship for the various components of the invention described above and in FIGS.

1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A catheter canal comprising
   a guiding structure, a plurality of flexible structures, and an adhesive structure;
   wherein the plurality of flexible structures and the adhesive structure attach to the guiding structure;
   wherein the catheter canal is a medical device;
   wherein the catheter canal is configured for use with a catheter;
   wherein the catheter canal forms a canal that is configured to control and limit movement of the catheter;
   wherein the plurality of flexible structures form a framework that creates the canal that is configured to control and limit movement of the catheter;
   wherein the adhesive structure secures the catheter canal in a fixed position during a medical procedure;
   wherein the guiding structure is a flexible structure with an inelastic nature;
   wherein the guiding structure forms containment surfaces of the canal that is configured to control and limit movement of the catheter;
   wherein each of the plurality of flexible structures is a semi-rigid mechanical structure, a flexible structure with an inelastic nature, or is deformed to form a u-shaped structure;
   wherein the guiding structure comprises a sheeting structure and a c-channel;
   wherein the adhesive structure is configured to removably attach the c-channel of the guiding structure to a surface such that the canal is configured to control and limit movement of the catheter so that the catheter will not shift during a medical procedure;
   wherein the sheeting structure is a flexible structure with an inelastic nature;
   wherein the sheeting structure physically forms the containment surfaces of the canal that is configured to control and limit movement of the catheter.

2. The catheter canal according to claim 1
   wherein the plurality of flexible structures forms a framework that shapes the c-channel formed by the guiding structure;
   wherein the c-channel is a mechanical structure that forms physical individual flexible structures;
   wherein the plurality of flexible structures are deformed such that the sheeting structure is shaped into boundary structures of the c-channel formed by the guiding structure.

3. The catheter canal according to claim 2
   wherein the adhesive structure is a removable adhesive compound;
   wherein the adhesive structure forms a coating on the attachment surface of the sheeting structure of the guiding structure.

4. The catheter canal according to claim 3 wherein the sheeting structure attaches to the plurality of flexible structures such that the plurality of flexible structures shapes the sheeting structure into the c-channel.

5. The catheter canal according to claim 4 wherein the sheeting structure is cut into the shape of a tapered structure.

6. The catheter canal according to claim 5 wherein each of the plurality of flexible structures attaches to a face of the sheeting structure.

7. The catheter canal according to claim 6
   wherein the sheeting structure comprises a channel surface, an attachment surface, a major axis, and a minor axis;
   wherein the channel surface is the surface of the sheeting structure that is configured to be proximal to the catheter;
   wherein the channel surface forms the interior surface of the canal formed by the c-channel;
   wherein the attachment surface is the surface of the c-channel that is distal from the channel surface;
   wherein the attachment surface forms the exterior surface of the canal formed by the c-channel;
   wherein the major axis is the major axis of the tapered structure form of the sheeting structure;
   wherein the major axis bisects a space between an edge of a perimeter of the sheeting structure with a greatest span of length and an edge of a perimeter of the sheeting structure that is distal from the edge of the perimeter of the sheeting structure with the greatest span of length;
   wherein the minor axis is the minor axis of the tapered structure form of the sheeting structure.

8. The catheter canal according to claim 7 wherein each of the plurality of flexible structures attaches to a face of the sheeting structure selected from the group consisting of the channel surface and the attachment surface.

9. The catheter canal according to claim 8
   wherein the plurality of flexible structures comprises a collection of individual flexible structures;
   wherein each of the individual flexible structure is a metal wire structure;
   wherein each of the individual flexible structure is a flexible structure with an inelastic nature; and
   wherein each of the individual flexible structure selected from the plurality of flexible structures is identical.

10. The catheter canal according to claim 9
    wherein each individual flexible structure is deformed into a u-shaped structure such that the individual flexible structure will deform the sheeting structure in a manner that forms the boundaries of the c-channel formed by the guiding structure;
    wherein each individual flexible structure attaches to the guiding structure such that a center axis of the prism structure of the individual flexible structure is perpendicular to the major axis of the sheeting structure.

11. The catheter canal according to claim 10
    wherein the individual flexible structure comprises a first arm, a second arm, and a crossbeam;
    wherein the first arm and the second arm attach to the crossbeam in the manner of a cantilever.

12. The catheter canal according to claim 11
    wherein the first arm is a prism-shaped structure;
    wherein the first arm is a first arm of the u-shaped structure;
    wherein the second arm is a prism-shaped structure;
    wherein the second arm is a second arm of the u-shaped structure.

13. The catheter canal according to claim 12
wherein the position of the first arm is set such that the free end of the cantilever structure of the first arm is proximal to the edge of the perimeter of the sheeting structure with the greatest span of length;
wherein the position of the second arm is set such that the free end of the cantilever structure of the second arm is proximal to the edge of the perimeter of the sheeting structure that is distal from the edge of the perimeter of the sheeting structure with the greatest span of length.

14. The catheter canal according to claim 13
wherein the crossbeam is a prism-shaped structure;
wherein the crossbeam attaches to the sheeting structure such that a center axis of the prism structure of the crossbeam is perpendicular to the major axis of the sheeting structure;
wherein the crossbeam attaches to the sheeting structure such that the center axis of the prism structure of the crossbeam is parallel to the minor axis of the sheeting structure.

15. The catheter canal according to claim 14
wherein the sheeting structure is formed as a fluid impermeable structure;
wherein the sheeting structure is formed from a polyurethane.

\* \* \* \* \*